United States Patent
Konstorum et al.

(10) Patent No.: US 6,485,411 B1
(45) Date of Patent: Nov. 26, 2002

(54) ENDOSCOPE SHAFT WITH SUPERELASTIC ALLOY SPIRAL FRAME AND BRAID

(75) Inventors: Gregory S. Konstorum, Stamford, CT (US); Edward A. Grabover, Danbury, CT (US)

(73) Assignee: Circon Corporation, Southborough, MA (US)

( * ) Notice: Subject to any disclaimer, the term of this patent is extended or adjusted under 35 U.S.C. 154(b) by 0 days.

(21) Appl. No.: 09/547,686

(22) Filed: Apr. 12, 2000

(51) Int. Cl.[7] .............................................. A61B 1/005
(52) U.S. Cl. ....................... 600/139; 600/140; 600/143; 604/527
(58) Field of Search ................................ 600/139–143; 604/95.01, 95.04, 95.05, 264, 523, 524, 525, 526, 527, 530, 531

(56) References Cited

U.S. PATENT DOCUMENTS

| | | |
|---|---|---|
| 4,580,551 A | 4/1986 | Siegmund et al. |
| 4,802,461 A | 2/1989 | Cho |
| 5,325,845 A | 7/1994 | Adair |
| 5,482,029 A * | 1/1996 | Sekiguchi et al. .......... 600/109 |
| 5,483,951 A | 1/1996 | Frassica et al. ............. 600/104 |
| 5,681,263 A | 10/1997 | Flesch ......................... 600/141 |
| 5,873,817 A | 2/1999 | Kokish et al. ............... 600/143 |
| 5,873,866 A * | 2/1999 | Kondo et al. ............... 600/140 |
| 5,927,345 A * | 7/1999 | Samson ....................... 138/123 |
| 5,938,588 A | 8/1999 | Grabover et al. ........... 600/150 |

FOREIGN PATENT DOCUMENTS

| | | | |
|---|---|---|---|
| GB | 2 130 885 | 6/1984 | |
| JP | 9-24019 | * 1/1997 | ............ A61B/1/00 |

* cited by examiner

*Primary Examiner*—John Mulcahy
(74) *Attorney, Agent, or Firm*—Harrington & Smith, LLP

(57) ABSTRACT

An endoscope having a control section and a shaft extending from the control section. The shaft comprises an outer cover; a tubular braid member located, at least partially, inside the outer cover; and a support frame located, at least partially, inside the tubular braid member. The support frame comprises a shape memory member which is spiral shaped. The shape memory member is comprised of a superelastic shape memory alloy. A first length of the support frame comprises the shape memory member having a first width and/or thickness a second length of the tubular shape comprises the shape memory member having a different second width and/or thickness such that the support frame has different respective stiffnesses along the first and second lengths.

32 Claims, 2 Drawing Sheets

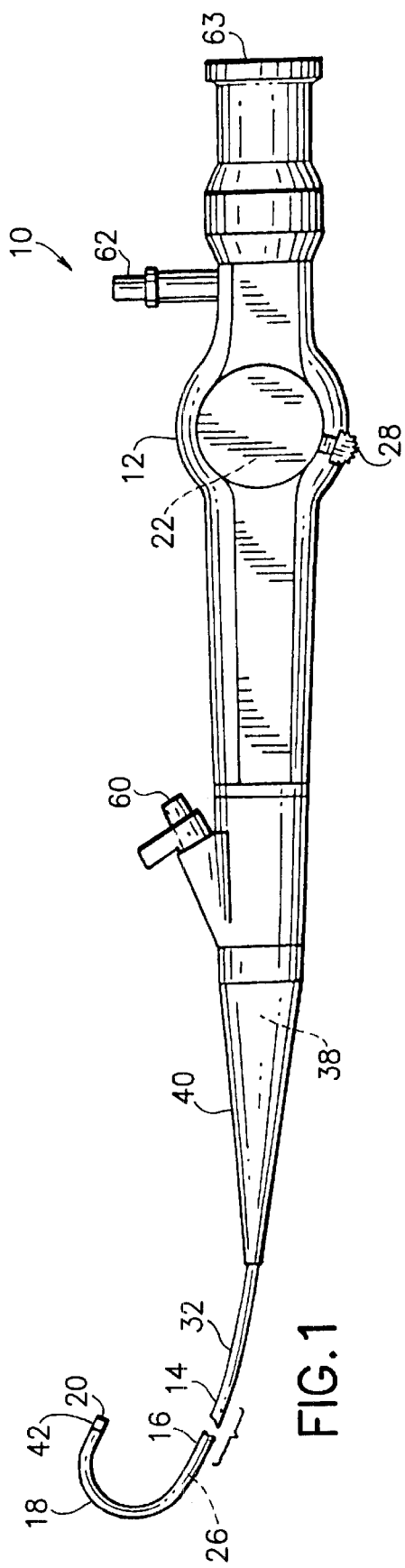
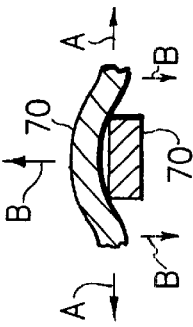
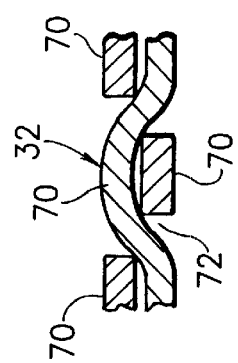
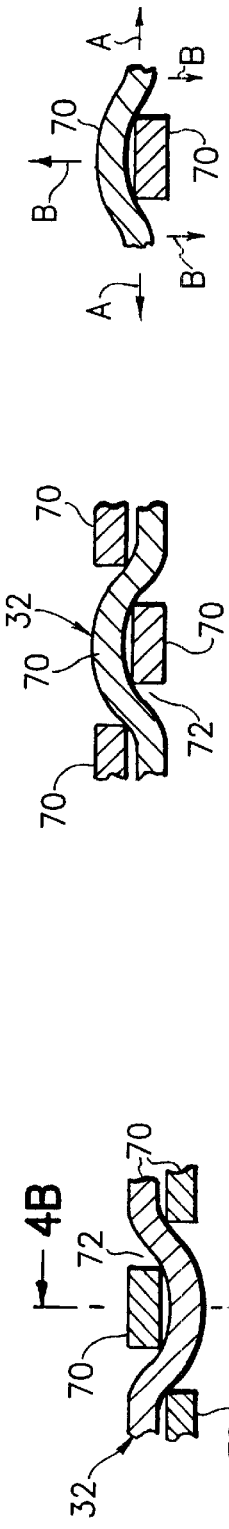

ENDOSCOPE SHAFT WITH SUPERELASTIC ALLOY SPIRAL FRAME AND BRAID

BACKGROUND OF THE INVENTION

1. Field of the Invention

The present invention relates to medical instruments and, more particularly, to an endoscope.

2. Prior Art

U.K. Patent Application No.2130885 discloses a flexible distal end portion for an endoscope. The end portion is made from plastic material with vertebrae connected by an elongate member or spine. U.S. Pat. No. 5,938,588 discloses an endoscope with wire sheaths made as solid tubes from a superelastic alloy material.

SUMMARY OF THE INVENTION

In accordance with one embodiment of the present invention, an endoscope is provided having a control section and a shaft extending from the control section. The shaft comprises an outer cover; a tubular braid member located, at least partially, inside the outer cover; and a support frame located, at least partially, inside the tubular braid member. The support frame comprises a shape memory member which is spiral shaped. The shape memory member is comprised of a superelastic shape memory alloy. A first length of the support frame comprises the shape memory member having a first width and a second length of the tubular shape comprises the shape memory member having a different second width such that the support frame has different respective stiffnesses along the first and second lengths.

In accordance with another embodiment of the present invention, an endoscope is provided having a control section and a shaft extending from the control section. The shaft comprises a front end member; a rear end member; a support frame connecting the front end member to the rear end member; and a tubular braid member surrounding the support frame. The tubular braid member is comprised of interwoven thread members comprised of superelastic shape memory alloy. The tubular braid member is heat treated to memorize home shapes of the thread members and the tubular braid member is then subsequently elongated and fixedly attached to the front and rear members with the thread members being elastically deformed towards a straightened shape.

In accordance with one method of the present invention, a method of manufacturing an endoscope shaft is provided comprising steps of providing a member comprised of superelastic shape memory alloy; forming the member into a support frame having a general spiral shape, wherein a first length of the support frame has spiral sections which each have a first width measured along an axis of the spiral shape and a second length of the member has spiral sections which each have a second different width measured along the axis of the spiral shape; connecting the support frame to a front end member and a rear end member; and connecting a Lubular shaped braid member to the first and second members over the support frame.

BRIEF DESCRIPTION OF THE DRAWINGS

The foregoing aspects and other features of the present invention are explained in the following description, taken in connection with the accompanying drawings, wherein:

FIG. 1 is a side elevational view of an endoscope incorporating features of the present invention;

FIG. 4A is a partial cross-sectional view of the braid member shown in FIG. 2 with the threads of the braid member at home positions;

FIG. 4B is a partial cross-sectional view of the braid member shown in FIG. 4A taken along line 4B—4B; and FIG. 4C is a partial cross-sectional view of the braid member shown in FIG. 4B when being elongated with the threads being moved towards straightened positions from their home positions.

DETAILED DESCRIPTION OF THE PREFERRED EMBODIMENT

Figure 2:
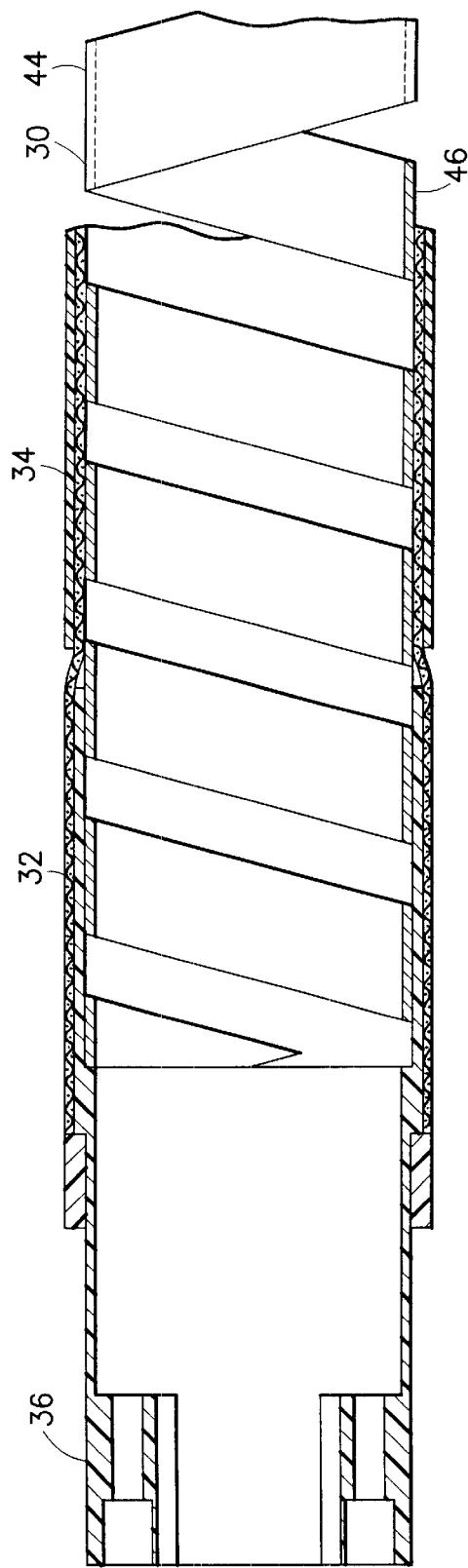
FIG. 2 is a partial cross-sectional view of some of the components of the shaft of the endoscope shown in FIG. 1.

Referring to FIG. 1, there is shown a side elevational view of an endoscope 10 incorporating features of the present invention. Although the present invention will be described with reference to the single embodiment shown in the drawings, it should be understood that the present invention can be embodied in many alternate forms of embodiments. In addition, any suitable size, shape or type of elements or materials could be used.

The endoscope 10 generally comprises a handle or control section 12 and a flexible or semi-flexible shaft 14 connected to the handle 12. The shaft 14 includes a passive deflection section 16 and an active deflection section 18 at the distal end of the shaft 14. A control system 22, to control the active deflection section 18, extends from the handle 12 to the active deflection section 18. The control system 22 generally comprises control wires and two wire sheaths (not shown), and an actuator 28. The wires are connected to the actuator 28 at one end and are connected to the active deflection section 18 at a second end. However, any suitable control system could be provided.

In the preferred embodiment, the actuator 28 comprises a user operated slide or lever. The actuator 28 is adapted to pull and release the two wires of the control system 22. The actuator 28 may also comprise a drum or pulley rotatably connected to the handle 12 to pull one wire while releasing the other. In an alternate embodiment, the actuator may be any suitable type of device, such as a rocker arm adapted to pull and release the wires of the control system 22. In another alternate embodiment, where the control system may have two or more pairs of control wires, the handle can have additional actuators and corresponding controls to drive the additional pairs of control wires. In still other alternate embodiments, the handle may have knobs with rack and pinion mechanisms or other suitable user operated controls for the control system.

The shaft 14 is cantilevered from the handle 12. In the preferred embodiment, the flexible shaft 14 has about an 8 Fr diameter. In alternate embodiments, the flexible shaft could have any suitable diameter. The flexible shaft 14 includes the control wires of the control system 22, a fiber optical image bundle (not shown), a fiber optical illumination bundle (not shown), and a working channel (not shown), similar to those shown in U.S. Pat. No. 5,938,588 which is hereby incorporated by reference in its entirety. A port 60 for inserting instruments (not shown) into the working channel is located on the handle 12. The handle 12 also has a light source post 62 for connecting a light source (not shown) to the illumination bundle. In addition, the handle 12 has an eyepiece 63 for a user to view an image transmitted by the image bundle from the front end 20. In alternate embodiments, the flexible shaft may house different and/or additional systems within.

Referring also to FIG. 2 a partial cross-sectional view of some of the components of the shaft 14 is shown. The shaft 14 generally comprises a support frame 30, a tubular braid member 32, a cover 34, a front end member 36, and a rear end member 38 (see FIG. 1). The rear end member 38 is a rigid member which is fixedly connected to the handle 12 and covered by a cone shaped elastic sleeve 40 which can function as a strain relief. The front end member 36 is also preferably a rigid member which has the stops for the wire sheaths and openings for the control wires, optical bundles and working channel connected to it. The outer end of the front end member forms the end 20 which forms the objective head 42 for the endoscope 10. The support 30 structurally connects the front end member 36 to the rear end member 38. The braid member 32 surrounds the support frame 30. Opposite ends of the braid member 32 are fixedly connected to the front end member 36 and rear end member 38, such as with adhesive, solder or welding. The cover 34 is preferably comprised of a polymer material and surrounds the braid member 32.

Figure 3:
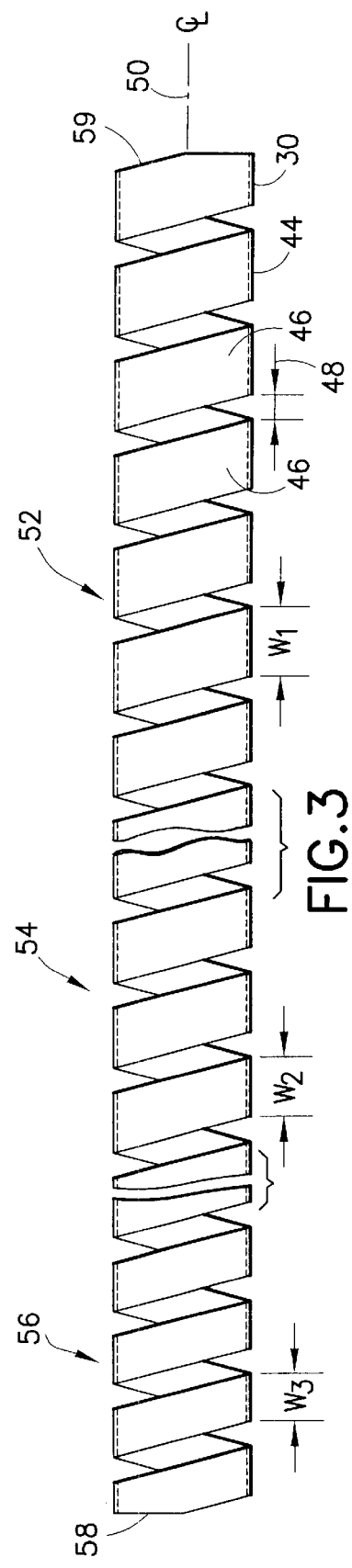
FIG. 3 is a side elevational view of the frame member of the shaft shown in FIG. 2.

Referring also to FIG. 3, in this embodiment the support frame 30 generally comprises a frame member 44 which is spiral shaped to provide a general tube configuration. In this embodiment the frame member 44 is provided as a single one-piece member. However, in alternate embodiments the frame member 44 could be comprised of multiple members. In a preferred embodiment the frame 30 also comprises a second frame member (not shown) which is attached to the front end 58 of the frame member 44 for use at the active deflection area 18. In this preferred embodiment the second frame member is a tube of superelastic material with multiple slots into the tube through a lateral side of the tube, such as disclosed in U.S. patent application Ser. No. 09/427,164 filed Oct. 26,1999 which is hereby incorporated by reference in its entirety. The second frame member could be attached to the first frame member 44 by any suitable means, such as a coupling tube (not shown). In an alternate embodiment features of the first and second frame members could be formed in a single one piece superelastic tube with multiple laterally inward extending slots into the tube along one length of the tube (for use at the active deflection section) and a spiral slot along another length of the tube (for use behind the active deflection section). In other alternate embodiments, the frame member 44 could be used with any other suitable frame member(s), or without any other frame member.

The frame member 44 is preferably comprised of a shape memory alloy material, such as Tinel or Nitinol. The shape memory alloy material is used for its superelastic properties exhibited by the material's ability to deflect and resiliently return to its natural or predetermined position even when material strains approach 4%, or an order of magnitude greater than the typical yield strain of 0.4% giving rise to plastic deformation in common metals. Thus, the term"superelastic alloy" is used to denote this type of material. The wire sheaths (not shown) may also be comprised of this type of material, such as disclosed in U.S. Pat. No. 5,938,588.

In this embodiment the frame member 44 comprises adjacent spiral sections 46 with a gap or spacing 48 between the sections 46. In a preferred embodiment the gap 48 is substantially the same or uniform along the length of the frame member 44. However, in alternate embodiments different size gaps could be provided along different section lengths of the frame member 44. The sections 46 have a general cross-sectionally flat shape as seen in FIG. 2. However, in an alternate embodiment the cross- sectional shape could be any suitable shape, such as round. A flat cross-sectional shape is preferred in order to minimize the diameter of the shaft 14 while keeping the area inside the frame member 44 as large as possible. In this embodiment the width of the frame member 44, measured at sections 46 parallel to the central axis 50 of the frame member's general spiral tube shape, is not the same along the length of the frame member 44. In this embodiment the frame member 44 has three section lengths 52, 54, 56 which each have sections 46 with different respective widths $W_1$, $W_2$, $W_3$. However, in alternate embodiments the widths could be the same, such as when the size of the gap 48 is different along different section lengths, and/or the frame member could have more or less than three section lengths with more or less than three respective widths, and/or one or more section lengths could have a varying spiral section width, such as the width of the sections 46 gradually decreasing along a length of the frame member from a rear direction to a front direction. In one embodiment the gap 48 is about 0.006–0.008 inch, length of section 52 is about 15.8 inches, $W_1$, is about 0.25 inch, length of section 54 is about 8.7 inches, $W_2$ is about 0.19 inch, length of section 56 is about 1.5 inches, $W_3$ is about 0.08 inch, wall thickness 58 is about 0.006 inch, and the inner diameter is about 0.088 inch. However, any suitable dimensions and/or lengths could be provided.

The purpose of providing the frame member 44 with different shaped sections 52, 54, 56 is to provide the frame member 44 with different stiffness properties at the different section lengths. This is somewhat analogous to the different section lengths described in U.S. patent application Ser. No. 09/427,164. The front section 56 is provided at the passive deflection section 16 of the shaft 14. Because the width $W_3$ is preferably the smallest of all the section lengths, the front section has the least stiffness of all the section lengths. The following section 54 has the width $W_2$ is preferably larger than the width $W_3$. Therefore, the section 54 has a larger stiffness than the section 56. The next section 52 is provided along a majority of the length of the shaft. Because the width $W_1$, is preferably larger than $W_2$, the section 52 has an even larger stiffness than the section 54. This larger stiffness provides sufficient rigidity to allow the user to push the shaft 14 through a small channel, such as a urethra. The front end 58 is stationarily attached to one front end member 36. The rear end 59 is stationarily attached to the rear end member 38.

The frame member 44 can provide the shaft 14 with a longer working life than conventional stainless steel frame members. One problem that can occur with endoscope shafts is that they can be accidentally crushed. A spiral coiled frame member made of stainless steel in the prior art could be permanently deformed by such a crushing force. However, the frame member 44, when made of a superelastic alloy, can resiliently deform under accidental crushing loads and return to its original shape without permanent deformation.

The braid member 32 has a general tubular shape and is comprised of interwoven threads 70 (see FIGS. 4A and 4B). In a preferred embodiment the threads 70 are comprised of flat strips or wires. However, the threads could have any suitable shape, such as round or oval. In a preferred embodiment the threads 70 are comprised of a superelastic alloy, such as Tinel or Nitinol. However, any suitable material could be used. The front end of the braid member 32 is stationarily attached to the front end member 36. The rear end of the braid member 32 is stationarily attached to the rear end member 38. The braid member 32 is located around the frame member 44 along the length of the frame member 44. The two members 32, 44 are preferably able to move relative to each other. The braid member 32 is primarily provided to increase resistance to deformation of the shaft due to torque. In other words, the braid member adds torque stability to the shaft 14.

Referring also to FIGS. 4A and 4B, when the braid member is comprised of a shape memory alloy, after the braid member 32 is woven, such as on a core, it is then heat treated in order to have the threads 70 memorize their shapes as home positions. The thickness of the braid member is only about 2.2 times the wall thickness of the threads 70. In a preferred embodiment the threads are about 0.001 inch thick, but any suitable thickness could be provided. The braid member 32 is heat treated while the braid member is at a first longitudinal length; which might be slightly tensioned along its longitudinal axis. After the braid member 32 is heat treated, it is then attached to the front and rear members 36, 38. During this attachment, the braid member 32 is elongated or stretched to a second longitudinal length. The second length is longer than the first length. This preloads the threads against each other. The frame member 44 is longitudinally compressed and then subsequently expands to put tension on the braid member 32 with the frame member 44 self-adjusting. With the memorized home positions as seen in FIGS. 4A and 4B, the home positions comprise the threads 70 having a general wavy shape along their lengths. Recesses 72 formed by the waves of the wavy shape form thread receiving areas. As seen with reference to FIG. 4C, when the braid member 32 is stretched during attachment to the end members 36, 38, the threads 70 are pulled in directions A towards straightened position relative to their home positions. However, because of the shape memory memorized home positions of the threads 70, internal forces from within the individual threads exert forces as indicated by arrows B to return back towards their home shapes as seen in FIGS. 4A and 4B. Unlike braid members in the prior art which were made from stainless steel, the recesses 72 are more pronounced (i.e.: deeper and narrower) and, thus, are more closely Shaped to the cross-sectional shape of the threads 70 in the recesses 72.

This embodiment provides the advantage of less movement between the threads 70 (i.e.: less sliding or shifting with an increased torque resistance as well as an increased column strength of the braid member 32. Compared to a prior art stainless steel braid member, the braid member of the present invention can provide an increase of torque resistance of about 30–35% and an increase in column strength of about 50%. In addition, unlike a stainless steel braid, even if the braid 32 is crimped during manufacture, it can return back to its original shape without permanent deformation. The braid 32 will also have a longer working life than a stainless steel braid. The braid 32 also will return to its home shape even if the shaft is accidentally crushed; whereas a stainless steel braid could have permanent deformation if its shaft was crushed. Although the present invention has been described above as being a shaft which comprises both a superelastic alloy frame member 44 and a superelastic alloy braid member 32, features of the present invention could be used with a stainless steel spiral frame member and the superelastic alloy braid member 32, or the superelastic alloy frame member 44 and a stainless steel braid member.

The frame member 44 could be manufactured in any one of a number of ways. One method of manufacturing the frame member 44 can comprise providing a solid tube of superelastic alloy (the tube having a hollow center) and then transforming the tube into the spiral shape. The step of transforming can comprise forming or creating spiral gap 48 through the wall of the tube along the length of the tube. The spiral gap could be formed by any suitable means, such as by cutting or burning through the tube with a laser or by using an electrical discharge machine (EDM) to cut or burn through the tube. The forming apparatus would preferably be computer controlled. The width of the gap 48 could be cut as a uniform width (with use of a uniform laser beam width or EDM width). The width of the gap 48 could also be non-uniform along the length of the tube. The computer controller could move the tube relative to the cutter (both longitudinally and rotationally) in a preprogrammed pattern to form the different sections along the length of the tube having different width spiral sections 46 and, thus, different flexibilities. The method could also comprise reducing the wall thickness of the tube at predetermined locations, such as grinding the outer perimeter of the tube, to further reduce stiffness at the predetermined locations. Another method of manufacturing the frame member 44 could include providing a strip of flat superelastic alloy, wrapping the strip in a spiral shape around a form, and then heat treating the strip to have the strip memorize the spiral shape due to its shape memory properties. These are just some examples. Any suitable method(s) could be used.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An endoscope having a control section and a shaft extending from the control section, the shaft comprising:
   an outer cover;
   a tubular braid member located, at least partially, inside the outer cover; and
   a support frame located, at least partially, inside the tubular braid member, the support frame comprising a shape memory member which is spiral shaped, wherein the shape memory member is comprised of a superelastic shape memory alloy, and wherein a first length of the support frame comprises the shape memory member having a first width and a second length of the support frame comprises the shape memory member having a different second width such that the support frame has different respective stiffnesses along the first and second lengths.

2. An endoscope as in claim 1 wherein the shape memory member comprises a cross-sectionally flat shape.

3. An endoscope as in claim 1 wherein a third length of the support frame comprises the shape memory member having a third width which is different than the first and second widths.

4. An endoscope as in claim 1 wherein a spiral gap spacing is provided between adjacent spiral sections of the shape memory member.

5. An endoscope as in claim 4 wherein the spiral gap spacing is substantially uniform along both the first and second lengths.

6. An endoscope as in claim 4 wherein the shape member comprises a tube member with the spiral gap spacing being laser cut or electrical discharge machined into the tube member.

7. An endoscope as in claim 1 wherein the shape memory member comprises a strip which is formed into the spiral shape and heat treated to shape memory memorize the spiral shape.

8. An endoscope as in claim 1 wherein the tubular braid member comprises interwoven thread members comprised of superelastic shape memory alloy.

9. An endoscope as in claim 1 wherein the shape memory member comprises at least two sections having.

10. An endoscope as in claim 1 wherein the spiral shape of the support frame extends along a majority of the support frame.

11. An endoscope as in claim 1 wherein the support frame comprises the shape memory member as a first shape memory member and further comprises a second shape memory member comprised of superelastic shape memory alloy, the second shape memory member being attached to a front end of the first shape memory member, and wherein the second shape memory member comprises a tubular shape with slots in different directions into lateral sides of the second shape memory member, the tubular shape having a center aperture occupying a majority of a cross-sectional area of the tubular shape.

12. An endoscope having a control section and a shaft extending from the control section, the shaft comprising:
    an outer cover;
    a tubular braid member located, at least partially, inside the outer cover; and
    a support frame located, at least partially, inside the tubular braid member, the support frame comprising a shape memory member which is spiral shaped, wherein the shape memory member is comprised of a superelastic shape memory alloy, and wherein a first length of the support frame comprises the shape memory member having a first width and a second length of the tubular shape comprises the shape memory member having a different second width such that the support frame has different respective stiffnesses along the first and second lengths, wherein the tubular braid member comprises interwoven thread members comprised of superelastic shape memory alloy, wherein the tubular braid member is heat treated at a first longitudinal length for the thread members to memorize their shapes while at the first longitudinal length and the tubular braid member is attached over the support frame as a second longer longitudinal length.

13. An endoscope having a control section and a shaft extending from the control section, the shaft comprising:
    a front end member;
    a rear end member;
    a support frame connecting the front end member to the rear end member; and
    a tubular braid member surrounding the support frame, the tubular braid member being comprised of interwoven thread members comprised of superelastic shape memory alloy, wherein the tubular braid member is heat treated to memorize home shapes of the thread members and the tubular braid member is then subsequently elongated and fixedly attached to the front and rear members with the thread members being elastically deformed towards a straightened shape.

14. An endoscope as in claim 13 wherein the thread members comprise flat wires having a general cross-sectionally flat shape.

15. An endoscope as in claim 13 wherein a wall thickness of the tubular braid member is about 2.2 times or less a wall thickness of the thread members.

16. An endoscope as in claim 13 wherein the memorized home shapes of the thread members comprise a wavy shape along their lengths, wherein recesses formed by waves of the wavy shape form thread receiving areas, and wherein a height of the thread receiving areas is about the same as a thickness of the thread members.

17. An endoscope as in claim 13 wherein the support frame comprises a spiral riember made of a super-elastic shape memory alloy.

18. An endoscope as in claim 17 wherein the spiral member comprises at least two section lengths with two respective different wall widths of the spiral member measured parallel to an axis of the spiral shape.

19. A method of manufacturing an endoscope shaft comprising steps of:
    providing a member comprised of superelastic shape memory alloy;
    forming the member into a support frame having a general spiral shape, wherein a first length of the support frame has spiral sections which each have a first width measured along an axis of the spiral shape and a second length of the member has spiral sections which each have a second different width measured along the axis of the spiral shape;
    connecting the support frame to a front end member and a rear end member; and
    connecting a tubular shaped braid member to the front and rear end members over the support frame.

20. A method as in claim 19 wherein the step of providing comprises providing the member as a solid tube and the step of forming comprises forming a spiral gap through the tube along the tube.

21. A method as in claim 20 wherein the spiral gap is formed by laser cutting through the tube.

22. A method as in claim 20 wherein the spiral gap is formed by electrical discharge machine cutting through the tube.

23. A method as in claim 1 wherein the step of providing comprises providing the member as a strip and the step of forming comprises wrapping the strip in the spiral shape with a form and heat treating the strip to shape memory memorize the spiral shape.

24. A method as in claim 19 further comprising reducing a wall thickness of the member along at least one section length of the support frame.

25. A method as in claim 19 wherein the step of forming forms the member in the spiral shape with a uniform gap spacing between adjacent ones of the spiral sections of the member.

26. A method as in claim 19 wherein the step of forming the member into the support frame comprises forming the general spiral shape along a majority of length of the support frame.

27. A method as in claim 19 further comprising connecting a second shape memory member to a front end of the general spiral shape between the general spiral shape and the front end member, the second shape memory member comprising a tubular shape with slots in different directions into lateral sides of the second shape memory member, the tubular shape having a center aperture occupying a majority of a cross-sectional area of the tubular shape.

28. A method of manufacturing a tubular braid member for use in an endoscope shaft comprising steps of:
    weaving thread members into a general tubular woven shape, the thread members being comprised of super elastic shape memory alloy; and
    heat treating the general tubular woven shape such that the thread members memorize a first wavy shape as home positions, wherein a longitudinal length of the tubular woven shape, when the tubular woven shape is heat treated, is provided as less than an intended longitudinal length of the tubular braid member when assembled into the endoscope shaft such that the tubular woven shape must be longitudinally lengthened when assembled into the endoscope shaft with the thread members being elastically deformed from their shape memory memorized home positions towards a straightened position, and wherein internal forces from within the thread members allow the thread members to individually resist being deformed from their memorized home positions.

29. In an endoscope having a control section and a shaft connected to the control section, the improvement comprising:

the shaft including a support frame comprising a first bendable frame member having a general tubular shape connected with a second frame member having a general tubular shape, wherein the second frame member is connected to a front end of the first frame member, and wherein the first frame member is comprised of super elastic material, is spiraled to form its general tubular shape, and is located along a majority of the length of the shaft, and the shaft further comprises a tubular braid member located over the first and second frame members.

30. An endoscope as in claim 20 wherein the shaft comprises an active deflection section operated by the control section and a passive deflection section, wherein the first frame member is located in the passive deflection section and the second frame member is located in the active deflection section.

31. An endoscope as in claim 30 wherein the second frame member comprises at least one tube of superelastic material with slots extending into at least one lateral side of the at least one tube.

32. An. endoscope as in claim 29 wherein the first frame member is spiraled along a majority of the first frame member's longitudinal length.

* * * * *